United States Patent
Curtis-Fisk et al.

(10) Patent No.: US 9,937,258 B2
(45) Date of Patent: *Apr. 10, 2018

(54) COMPOSITION FOR APPLICATION TO A NASAL MUCOSA COMPRISING A METHYLCELLULOSE

(71) Applicant: Dow Global Technologies LLC, Midland, MI (US)

(72) Inventors: Jaime L. Curtis-Fisk, Midland, MI (US); Susan L. Jordan, Doylestown, PA (US); True L. Rogers, Midland, MI (US); Matthias Knarr, Nienburg/Weser (DE); Meinolf Brackhagen, Walsrode (DE); Roland Adden, Bomlitz (DE)

(73) Assignee: Dow Global Technologies LLC, Midland, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 14/890,617

(22) PCT Filed: Jul. 16, 2014

(86) PCT No.: PCT/US2014/046809
§ 371 (c)(1),
(2) Date: Nov. 12, 2015

(87) PCT Pub. No.: WO2015/009796
PCT Pub. Date: Jan. 22, 2015

(65) Prior Publication Data
US 2016/0114047 A1   Apr. 28, 2016

Related U.S. Application Data

(60) Provisional application No. 61/847,228, filed on Jul. 17, 2013.

(51) Int. Cl.
| | |
|---|---|
| *A61K 47/38* | (2006.01) |
| *A61K 47/02* | (2006.01) |
| *A61K 31/167* | (2006.01) |
| *A61K 9/00* | (2006.01) |

(52) U.S. Cl.
CPC ............ *A61K 47/38* (2013.01); *A61K 9/0043* (2013.01); *A61K 31/167* (2013.01); *A61K 47/02* (2013.01)

(58) Field of Classification Search
CPC .... A61K 9/0043; A61K 31/167; A61K 47/38; A61K 47/302
See application file for complete search history.

(56) References Cited

U.S. PATENT DOCUMENTS

| | | | | |
|---|---|---|---|---|
| 6,235,893 B1* | 5/2001 | Reibert | ............... | C08B 11/02 264/140 |
| 2007/0297991 A1 | 12/2007 | Peyman | | |
| 2008/0112895 A1 | 5/2008 | Kottayil et al. | | |
| 2011/0269711 A1* | 11/2011 | Adden | ............ | A61K 9/0053 514/57 |
| 2012/0077836 A1* | 3/2012 | Wikstrom | ........... | A61K 9/0019 514/290 |

FOREIGN PATENT DOCUMENTS

| | | |
|---|---|---|
| CN | 101810562 | 8/2010 |
| CN | 102078266 | 6/2011 |
| EP | 0023359 A2 | 2/1981 |
| EP | 1681065 A1 | 7/2006 |
| EP | 1997483 | 12/2008 |
| WO | 2008042789 A1 | 4/2008 |
| WO | 2009046444 A2 | 4/2009 |
| WO | WO 2012051034 A1 * | 4/2012 |
| WO | 2013059064 A1 | 4/2013 |
| WO | 2013059065 A1 | 4/2013 |

OTHER PUBLICATIONS

Majithiya R. et al., Thermoreversible-mucoadhesive Gel for Nasal Delivery of Sumatriptan, AAPS PharmSciTech, 2006, 7, 3, Article 67, pp. 1-7.
Sweet D. et al., Quantitative Analysis by various G.L.C. Response-Factor Theories for partially Methylated and partially Ethylated Alditol Acetates, Carbohydrate Research, 40, 1975, pp. 217-225.
Lindberg et al., Distribution of Substituents in o-Ethyl-O-(2-Hydroxy-Ethyl) Cellulose, Carbohydrate Research, 176, 1988, pp. 137-144.
Addison et al., Flame Ionization Detector Molar Responses for Methyl Esters of Some Polyfunctional Metabolic Acids, Journal of Gas Chromatography, vol. 6, 1968, pp. 135-138.
Ackman R., Fundamental Groups in the Response of Flame Ionization Detectors to Oxygenated Aliphatic Hydrocarbons, Journal of Gas Chromatography, 1964, pp. 173-179 .
Technical handbook, Methocel cellulose ethers, XP-002629689.

* cited by examiner

*Primary Examiner* — Yanzhi Zhang

(57) ABSTRACT

A composition designed for application to a mucosa comprises a tonicity-adjusting agent, a methylcellulose, and a liquid diluent, wherein the methylcellulose has anhydroglucose units joined by 1-4 linkages wherein hydroxy groups of anhydroglucose units are substituted with methyl groups such that s23/s26 is 0.36 or less, wherein s23 is the molar fraction of anhydroglucose units wherein only the two hydroxy groups in the 2- and 3-positions of the anhydroglucose unit are substituted with methyl groups and wherein s26 is the molar fraction of anhydroglucose units wherein only the two hydroxy groups in the 2- and 6-positions of the anhydroglucose unit are substituted with methyl groups.

8 Claims, 1 Drawing Sheet

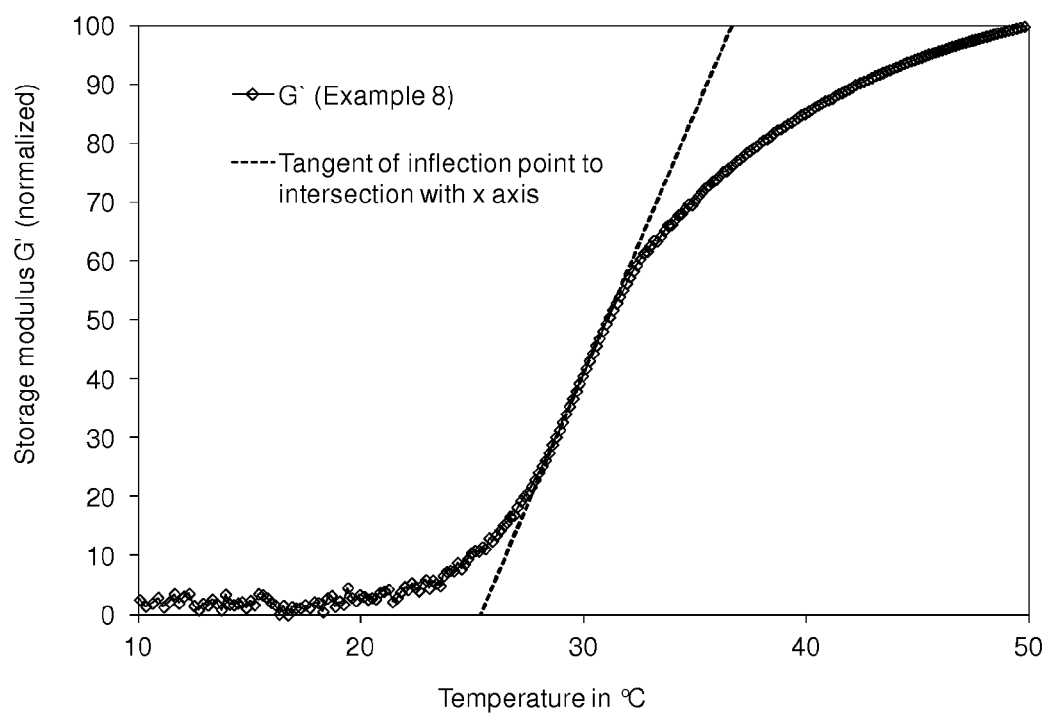

US 9,937,258 B2

COMPOSITION FOR APPLICATION TO A NASAL MUCOSA COMPRISING A METHYLCELLULOSE

FIELD

The present invention concerns a composition for application to a mucosa, e.g. for transmucosal delivery of a physiologically active agent, and a method of administering a physiologically active agent to an individual.

INTRODUCTION

Compositions for application to mucosae, such as pharmaceutical compositions for transmucosal delivery of physiologically active agents, have been known for a long time. Nasal drops and sprays have been known as drug delivery systems intended for administration to the nasal cavity. However, known nasal drops and sprays often rapidly exit the nasal cavity either via dripping from the nostrils or via the back of the nasal cavity into the nasopharynx, which can lead to insufficient efficacy of the physiologically active agent(s). High-viscosity delivery systems, such as ointments or gels, are retained in the nasal cavity for a longer time period, but the exact dosage of ointments and gels is difficult to meter and subsequently deliver to the desired location within the nasal cavity. Similar problems are experienced if pharmaceutical compositions are applied to other mucosae, such as the mucous membrane of the eyes or to mucosae in the oral cavity, such as the buccal mucosa.

To address this problem, European Patent EP 0 023 359 discloses a powdery pharmaceutical composition for application to the mucosa of the nasal cavity which comprises a drug and a carrier. At least 90% of the composition consists of particles having an effective particle diameter of 20 to 250 μm. The composition comprising a lower alkyl ether of cellulose having a viscosity, determined at 37° C.±0.2° C. for a 2% aqueous solution thereof, of 5 to 5000 mPa·s. The lower alkyl ether of cellulose is preferably methyl cellulose, hydroxypropyl cellulose or hydroxypropylmethyl cellulose. Those having a degree of ether substitution of 0.1 to 6, especially 0.4 to 4.6 are said to be preferred. The pharmaceutical composition absorbs mucus on the nasal mucosa and covers the nasal mucosa as a fluid surface. Unfortunately, spraying a powdery pharmaceutical composition into the nasal cavity is quite complex. The European Patent EP 023 359 suggests filling a capsule with the powdery composition, mounting it in a sprayer equipped by a needle, piercing the capsule with the needle to provide minute holes on the top and bottom sides of the capsule and thereafter sending air by means of a rubber ball to jet out the powder. Moreover, a powdery composition often gives the feel of foreign matter in the nasal cavity, irritates the nasal cavity and can lead to drying out of the nasal cavity.

In view of the above-mentioned deficiencies of the prior art compositions to be applied to a mucosa, the object of the present invention is to provide a composition that can be easily applied onto a mucosa, and that is retained on the mucosa for an extended time period.

SUMMARY

One aspect of the present invention is a composition for application to a mucosa which comprises a tonicity-adjusting agent, a methylcellulose, and a liquid diluent, wherein the methylcellulose has anhydroglucose units joined by 1-4 linkages wherein hydroxy groups of anhydroglucose units are substituted with methyl groups such that s23/s26 is 0.36 or less, wherein s23 is the molar fraction of anhydroglucose units wherein only the two hydroxy groups in the 2- and 3-positions of the anhydroglucose unit are substituted with methyl groups and wherein s26 is the molar fraction of anhydroglucose units wherein only the two hydroxy groups in the 2- and 6-positions of the anhydroglucose unit are substituted with methyl groups.

Another aspect of the present invention is a container which comprises the above-mentioned composition, wherein the container is designed for releasing the composition by spraying or as drops.

Yet another aspect of the present invention is a method of transmucosal administration of a physiologically active agent to an individual wherein the above-mentioned composition, that additionally comprises a physiologically active agent, is applied to a mucosa of the individual.

BRIEF DESCRIPTION OF DRAWINGS

FIG. 1 illustrates how to determine the gelation temperature of a composition of the present invention.

DESCRIPTION OF EMBODIMENTS

Surprisingly, it has been found that the composition of the present invention exhibits a gelation temperature of up to 37° C., typically up to 35° C., and more typically up to 33° C. The gelation temperature of the composition of the present invention is generally at least 18° C., typically at least 21° C., more typically at least 24° C., and most typically at least 27° C.

The composition of the present invention is very useful for application to a mucosa, e.g. for transmucosal delivery of a physiologically active agent. A low viscosity at 5° C. or 20° C., i.e., at a temperature at which the composition is usually stored and/or applied, facilitates the release of the composition from a container comprising such composition, e.g. as drops or by spraying, and the administration of the composition to a mucosa. The temperature of the composition increases after its application to a mucosa.

Thermal gelation at the gelation temperature of the composition of the present invention triggers two phenomena to maximize efficacy of the delivery system: 1) The high-viscosity major portion of the thermally gelled composition facilitates retention of the composition of the present invention on the mucosa. 2) Syneresis occurs upon thermal gelation of the composition of the present invention, and the methylcellulose, the tonicity-adjusting agent and the typically present physiologically active agent are concentrated into a syneresed layer most intimately interfacing with the mucosa instead of being rinsed off the mucosa in syneresis fluid.

Conventionally, methylcellulose has been found to be very useful in a variety of applications, providing thickening, freeze/thaw stability, lubricity, moisture retention and release, film formation, modified-release, texture, consistency, shape retention, emulsification, binding, gelation, and suspension properties. However, methylcellulose usually do not provide a sufficient thickening effect to compositions at temperatures encountered within the nasal cavities of mammals, such as those of human beings, as shown in the accompanying examples. One unusual property of methylcellulose is that it is known to exhibit reverse thermal gelation in water; in other words, methylcellulose gels at temperatures above 50° C. when dissolved at a concentration of 2% and forms a liquid if cooled again down to temperatures of 20° C. or less. Most grades of methylcellulose, dissolved alone to 2 wt. % in water at about 5° C., will gel at least about 10° C. higher than the normal body temperature of a human being.

In the present invention, a specific methylcellulose is an essential component of the composition for transmucosal delivery. The methylcellulose has anhydroglucose units joined by 1-4 linkages. Each anhydroglucose unit contains hydroxyl groups at the 2, 3, and 6 positions. Partial or complete substitution of these hydroxyls creates cellulose derivatives. For example, treatment of cellulosic fibers with caustic solution, followed by a methylating agent, yields cellulose ethers substituted with one or more methoxy groups. If not further substituted with other alkyls, this cellulose derivative is known as methylcellulose.

An essential feature of the specific methylcellulose used in the composition of the present invention is the position of the methyl groups. The composition for transmucosal delivery of the invention comprises a methylcellulose wherein hydroxy groups of anhydroglucose units are substituted with methyl groups such that s23/s26 is 0.36 or less, preferably 0.33 or less, more preferably 0.30 or less, most preferably 0.27 or less or 0.26 or less, and particularly 0.24 or less or 0.22 or less. Typically s23/s26 is 0.08 or more, 0.10 or more, 0.12 or more, 0.14 or more, or 0.16 or more.

In the ratio s23/s26, s23 is the molar fraction of anhydroglucose units wherein only the two hydroxy groups in the 2- and 3-positions of the anhydroglucose unit are substituted with methyl groups and s26 is the molar fraction of anhydroglucose units wherein only the two hydroxy groups in the 2- and 6-positions of the anhydroglucose unit are substituted with methyl groups. For determining the s23, the term "the molar fraction of anhydroglucose units wherein only the two hydroxy groups in the 2- and 3-positions of the anhydroglucose unit are substituted with methyl groups" means that the two hydroxy groups in the 2- and 3-positions are substituted with methyl groups and the 6-positions are unsubstituted hydroxy groups. For determining the s26, the term "the molar fraction of anhydroglucose units wherein only the two hydroxy groups in the 2- and 6-positions of the anhydroglucose unit are substituted with methyl groups" means that the two hydroxy groups in the 2- and 6-positions are substituted with methyl groups and the 3-positions are unsubstituted hydroxy groups.

Formula I below illustrates the numbering of the hydroxy groups in anhydroglucose units.

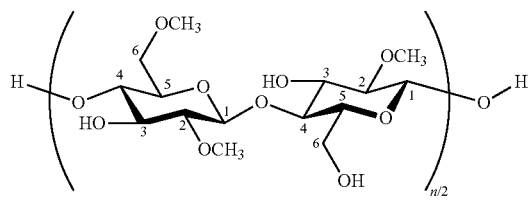

Formula I

In one embodiment of the invention hydroxy groups of anhydroglucose units are substituted with methyl groups such that the s23/s26 of the methylcellulose is 0.27 or less, preferably 0.26 or less, more preferably 0.24 or less or even 0.22 or less. In this embodiment of the invention s23/s26 of the methylcellulose typically is 0.08 or more, 0.10 or more, 0.12 or more, 0.14 or more, 0.16 or more, or 0.18 or more. Methods of making methylcelluloses of this embodiment are described in more detail in the Examples. A general procedure of making methylcelluloses of this embodiment is described in International Patent Applications WO 2013/059064, pages 11-12 and WO 2013/059065, pages 11-12, the teaching of which is incorporated herein by reference.

In another embodiment of the invention hydroxy groups of anhydroglucose units are substituted with methyl groups such that the s23/s26 of the methylcellulose is more than 0.27 and up to 0.36, preferably more than 0.27 and up to 0.33, and most preferably more than 0.27 and up to 0.30. Methylcelluloses wherein hydroxy groups of anhydroglucose units are substituted with methyl groups such that s23/s26 is about 0.29 are commercially available under the trade name METHOCEL SG or SGA (The Dow Chemical Company). They gel at a relatively low temperature, at 38° C. to 44° C. at a concentration of 2 wt. % in water. U.S. Pat. No. 6,235,893, the entirety of which is incorporated by reference herein, teaches the preparation of methylcelluloses of which 1.5 wt. % solutions in water exhibit onset gelation temperatures of 31-54° C., most of them exhibiting gelation temperatures of 35-45° C.

The methylcellulose preferably has a DS(methyl) of from 1.55 to 2.25, more preferably from 1.65 to 2.20, and most preferably from 1.70 to 2.10. The degree of the methyl substitution, DS(methyl), also designated as DS(methoxyl), of a methylcellulose is the average number of OH groups substituted with methyl groups per anhydroglucose unit.

The determination of the % methoxyl in methylcellulose is carried out according to the United States Pharmacopeia (USP 34). The values obtained are % methoxyl. These are subsequently converted into degree of substitution (DS) for methyl substituents. Residual amounts of salt have been taken into account in the conversion.

The viscosity of the methylcellulose is generally at least 2.4 mPa·s, preferably at least 3 mPa·s, and most preferably at least 10 mPa·s, when measured as a 2 wt. % aqueous solution at 5° C. at a shear rate of 10 s$^{-1}$. The viscosity of the methylcellulose is preferably up to 10,000 mPa·s, more preferably up to 5000 mPa·s, and most preferably up to 2000 mPa·s, when measured as indicated above.

Although the above-described specific methylcelluloses cause aqueous solutions to gel at a lower temperature than most known methylcelluloses, they are not always sufficiently effective at temperatures of up to 37° C. or even only up to 32° C. at low concentrations in aqueous solutions, e.g., at a concentration of 1 wt-% or less. The gelation temperature of an aqueous solution can be decreased by increasing the concentration of the methylcellulose, but this is not always desirable. Increasing the concentration of a given methylcellulose in an aqueous solution usually increases its viscosity at 5° C. or 20° C., which makes spraying or dropping the aqueous solution onto mucosa more difficult. Surprisingly, it has been found that the presence of a tonicity-adjusting agent lowers the gelation temperature of a composition comprising the above-described methylcellulose.

Accordingly, another essential ingredient of the composition of the present invention is a tonicity-adjusting agent. One or more tonicity-adjusting agents may be included in the composition of the present invention to partially or fully achieve tonicity with body fluids, e.g. fluids of the nasal cavity or fluids of the eye, resulting in reduced levels of irritation. Examples of pharmaceutically acceptable tonicity-adjusting agents include, but are not limited to, sodium chloride, potassium chloride, dextrose, xylitol, calcium chloride, glucose, glycerin, mannitol, and sorbitol. A tonicity-adjusting agent is preferably included in an amount of from 0.1 to 10 percent, more preferably from 0.2 to 8.0 percent, even more preferably from 0.3 to 6.0 percent, and most preferably from 0.5 to 4.0 percent, based on the total weight of the composition. In one embodiment, the tonicity-adjusting agent is dextrose and/or xylitol. In another embodiment, the tonicity-adjusting agent is sodium chloride. In yet another embodiment the tonicity-adjusting agent is a buffering agent. Suitable buffering agents include, but are not limited to, organic acid salts such as salts of citric acid, gluconic acid, carbonic acid, tartaric acid, succinic acid, acetic acid, phthalic acid, or phosphoric acid. A phosphate buffer is particularly useful. Phosphate buffers typically comprise sodium or potassium phosphate dibasic or sodium or potassium phosphate monobasic. In addition, amino acid components can also be used as buffering agent. Such amino acid component includes without limitation glycine and histidine. The buffering agent provides improved pH control. In one embodiment, the composition of the invention has a pH between 5.0 and 8.0, preferably between 6.0 and 8.0, and more preferably between 6.0 and 7.0. In a specific embodiment, a composition of the invention has a pH of about 6.5.

It has surprisingly been found that a composition of the present invention which comprises the methylcellulose described further above in combination with a tonicity-adjusting agent exhibits thermal gelation at a lower temperature than a comparable composition containing the same type and amount of methylcellulose without the tonicity-adjusting agent. Alternatively, a lower concentration of the afore-mentioned methylcellulose and/or an afore-mentioned methylcellulose having a lower viscosity (measured as a 2 wt-% solution in water at 20° C.) can be utilized in the presence of a tonicity-adjusting agent while still achieving thermal gelation of the composition at the desired temperature. The effects of the tonicity-adjusting agent in combination with the methylcellulose described further above are illustrated in more detail in the Examples.

The composition of the present invention is useful for application to mucosae, e.g., for intranasal, buccal, sublingual, vaginal, ocular or rectal application.

In one embodiment of the invention the composition comprises one or more physiologically active agents, preferably one or more drugs, one or more diagnostic agents, or one or more essential oils, or one or more physiologically active agents which are useful for cosmetic or nutritional purposes. The term "drug" denotes a compound having beneficial prophylactic and/or therapeutic properties when administered to an individual, typically a mammal, especially a human individual. Physiologically active agents that are useful for transmucosal delivery, such as intranasal, buccal, sublingual, vaginal, ocular or rectal delivery, or delivery through a mucosal membrane located on the gums or lips are known in the art.

The composition of the present invention is particularly useful for intranasal delivery of one or more physiologically active agents or for delivery through a mucosal membrane located in the oral cavity, such as drugs utilized in therapies for allergic rhinitis, nasal congestion and infections, in treatments of diabetes, migraine, nausea, smoking cessation, acute pain relief, nocturnal enuresis, osteoporosis, vitamin B-12 deficiency and for administering intranasal influenza vaccine, however the physiologically active agents are not limited to these examples. Especially preferred drugs are acetaminophen, azelastine hydrochloride, beclomethasone dipropionate monohydrate, sumatriptan succinate, dihydroergotamine mesylate, fluticasone propionate, triamcinolone acetonide, budesonide, fentanyl citrate, butorphanol tartrate, zolmitriptan, desmopressin acetate hydrate, salmon calcitonin, nafarelin acetate, buserelin acetate, elcatonin, oxytocin, insulin, mometasone furoate, estradiol, metoclopramide, xylometazoline hydrochloride, ipratropium bromide hydrate, olopatadine hydrochloride, oxymetazoline hydrochloride, dexpanthenol, hydrocortisone, naphazoline hydrochloride, phenylephrine hydrochloride, mepyramine maleate, phenylephrine hydrochloride, cromolyn sodium, levocabastine hydrochloride, vitamin B12, prednisolone sodium metasulphobenzoate, naphazoline nitrate, tetrahydrozoline hydrochloride, chlorpheniramine maleate, benzethonium chloride, ketotifen fumarate, histamine dihydrochloride, fusafungine, or combinations thereof. Examples of essential oils are menthol, methyl salicylate, thymol, eucalyptus oil, camphor, anise, sweet orange, or combinations thereof. It has surprisingly been found that the presence of certain physiologically active agents in the composition of the present invention can further reduce the temperature at which thermal gelation occurs.

In yet another embodiment of the invention the composition does not comprise a physiologically active agent that is selected from drugs, diagnostic agents, essential oils, or physiologically active agents which are useful for cosmetic or nutritional purposes. Compositions comprising an above-described methylcellulose in combination with a tonicity-adjusting agent but not a physiologically active agent in addition are useful, e.g., for rinsing and/or moisturizing the nasal cavity or as artificial tears.

The composition for transmucosal delivery further comprises a liquid diluent, of which at least 55 weight percent and up to 100 percent is water. The composition of the present invention may additionally comprise an organic liquid diluent; however, the composition of the present invention should comprise at least 55, preferably at least 65, more preferably at least 75, most preferably at least 90, and particularly at least 95 weight percent of water and up to 45, preferably up to 35, more preferably up to 25, most preferably only up to 10, and particularly only up to 5 weight percent of an organic liquid diluent, based on the total weight of the organic liquid diluent and water. In one embodiment the diluent consists of water. The water is typically a high-quality grade of water such as purified water, for example USP purified water, PhEur purified water or water for Injection (WFI).

The term "organic liquid diluent" as used herein means an organic solvent or a mixture of two or more organic solvents that is liquid at 25° C. and atmospheric pressure. Preferred organic liquid diluents are polar organic solvents having one or more heteroatoms, such as oxygen, nitrogen or halogen (like chlorine). More preferred organic liquid diluents are alcohols, for example multifunctional alcohols, such as propylene glycol, polyethylene glycol, polypropylene glycol and glycerol; or preferably monofunctional alcohols, such as ethanol, isopropanol or n-propanol; or acetates, such as ethyl acetate. More preferably the organic liquid diluents have 1 to 6, most preferably 1 to 4 carbon atoms. The organic liquid diluent is preferably pharmaceutically acceptable, such as ethanol or glycerol.

The composition of the present invention may comprise one or more optional adjuvants, such as one or more suspending agents, odor, flavor or taste improvers, preservatives, pharmaceutically acceptable surfactants, coloring agents, opacifiers, or antioxidants. Typically, pharmaceutically acceptable optional adjuvants are selected.

For stability purposes, compositions of the invention (for example intranasal compositions) may be protected from microbial or fungal contamination and growth by inclusion of one or more preservatives. Examples of pharmaceutically acceptable anti-microbial agents or preservatives may include, but are not limited to, quaternary ammonium compounds (e.g. benzalkonium chloride, benzethonium chloride, cetrimide, cetylpyridinium chloride, lauralkonium chloride and myristyl picolinium chloride), mercurial agents (e.g. phenylmercuric nitrate, phenylmercuric acetate and thimerosal), alcoholic agents (e.g. chlorobutanol, phenylethyl alcohol and benzyl alcohol), antibacterial esters (e.g. esters of para-hydroxybenzoic acid), chelating agents such as disodium edetate (EDTA) and other anti-microbial agents such as chlorhexidine, chlorocresol, sorbic acid and its salts (such as potassium sorbate) and polymyxin. Examples of pharmaceutically acceptable anti-fungal agents or preservatives may include, but are not limited to, sodium benzoate, sorbic acid, sodium propionate, methylparaben, ethylparaben, propylparaben and butylparaben. The preservative(s), if included, are typically present in an amount of from 0.001 to 1%, such as from 0.015% to 0.5%, based on the total weight of the composition. In one embodiment, the preservative is selected from benzalkonium chloride, EDTA and/or potassium sorbate. In a further embodiment, the preservative is EDTA and/or potassium sorbate.

Typically the composition of the present invention comprises from 0.1 to 20 percent, preferably from 0.2 to 15 percent, even more preferably from 0.5 to 10 percent, and most preferably from 0.5 to 8 percent of the methyl cellulose defined above, from 0.1 to 10 percent, more preferably from 0.2 to 8.0 percent, even more preferably from 0.3 to 6.0 percent, and most preferably from 0.5 to 4.0 percent of a tonicity-adjusting agent, from 0 to 20 percent, or from 0.01 to 10 percent, or from 0.1 to 5 percent of a physiologically active agent, and from 0 to 30 percent, or from 0.01 to 20 percent, or from 0.1 to 10 percent, of one or more optional adjuvants, based on the total weight of the composition, the remainder being a liquid diluent. At least 55 percent, preferably at least 65 percent, more preferably at least 75 percent, most preferably at least 90 percent, and particularly at least 95 percent, and up to 100 percent of the weight of the liquid diluent is water. The composition generally comprises a sufficient amount of liquid diluent that the composition is liquid at 5° C. Preferably, the amount of the liquid diluent is at least 50 percent, more preferably at least 80 percent, and most preferably at least 90 percent, based on the total weight of the composition. The composition of the present invention generally has a viscosity of from 2.4 to 10,000 mPa·s, preferably from 3 to 5000 mPa·s, even more preferably from 5 to 2000 mPa·s, and most preferably from 5 to 1500 mPa·s, measured at 5° C. at a shear rate of $10\ s^{-1}$. The composition of the present invention is preferably in the form of a sprayable solution or suspension, a solution or suspension to be applied as drops or in the form of a syrup. The composition can be packaged into suitable containers, which can also serve as delivery devices, e.g., containers designed for generating and subsequently applying sprays or drops to the intended delivery site. The delivery devices can be multi-dose or unit-dose devices.

The composition of the present invention is preferably packaged in a container such that the volume of the composition in the container is not more than 100 ml, more preferably not more than 50 ml or not more than 25 ml. Typically the volume of the composition in the container is at least 0.1 ml, or at least 1 ml, or at least 2 ml, or at least 5 ml, or at least 10 ml. The volume of the liquid composition typically depends on the intended use. Single-dose vials often comprise only 0.1-2 ml of a liquid composition. Sprays or bottles which are designed to release the composition drop by drop usually comprise larger amounts of the liquid composition, e.g., 5-50 ml or 10-25 ml.

The composition of the present invention is preferably stored at a temperature of from 1 to 23° C., more preferably from 5 to 20° C. Upon application of the composition of the present invention to a mucosa of an individual, the temperature of the composition increases and the methylcellulose suspended or, preferably, dissolved in the aqueous diluent of the composition gels when the temperature of the composition of the present invention adjusts to the temperature of the mucosa, i.e., to a temperature of 30-37° C., typically 30-35° C. The exact temperature of the mucosa somewhat depends on the type of mucosa, on the individual, on the time of day, and on the conditions of the surrounding environment. In the case of human beings the mucosa in the nasal cavity typically has a temperature of 30-35° C., the oral mucosa under the tongue typically has a temperature of about 36.8±0.4° C., and the rectal mucosa typically has a temperature of about 37° C.

The gelation of the composition can be determined as described in the Examples section. Due to its low gelation temperature, the composition of the present invention is particularly useful for application to the nasal mucosa. Generally, the composition of the present invention exhibits a gelation temperature of up to 37° C., typically up to 35° C., and more typically up to 33° C.

The gelation behavior of the methylcellulose utilized in the compositions of the present invention can be adapted to a certain degree to the specific need of a certain transmucosal delivery system. E.g., the desired viscosity increase of the composition of the present invention can be achieved at a lower temperature if a methylcellulose of higher viscosity grade, measured as a 2 weight-% solution in water at 20° C., is selected than when a methylcellulose of lower viscosity grade is selected.

Some embodiments of the invention will now be described in detail in the following Examples.

Examples 1-11 and Comparative Examples A-I

Unless otherwise mentioned, all parts and percentages are by weight. In the Examples the following test procedures are used.

Production of Methylcellulose MC-1 to MC-4

Methylcelluloses MC-1 to MC-4 were produced according to the following procedure. Finely ground wood cellulose pulp was loaded into a jacketed, agitated reactor. The reactor was evacuated and purged with nitrogen to remove oxygen, and then evacuated again. The reaction is carried out in two stages. In the first stage, a 50 weight percent aqueous solution of sodium hydroxide was sprayed onto the cellulose until the level reached 1.8 mol of sodium hydroxide per mol of anhydroglucose units of the cellulose, and then the temperature was adjusted to 40° C. After stirring the mixture of aqueous sodium hydroxide solution and cellulose for about 20 minutes at 40° C., 1.5 mol of dimethyl ether and 2.3 mol of methyl chloride per mol of anhydroglucose units were added to the reactor. The contents of the reactor were then heated in 60 min to 80° C. After having reached 80° C., the first stage reaction was allowed to proceed for 5 min. Then the reaction was cooled down to 65° C. in 20 min.

The second stage of the reaction was started by addition of methyl chloride in an amount of 3.4 molar equivalents of methyl chloride per mol of anhydroglucose unit. The addition time for methyl chloride was 20 min. Then a 50 weight percent aqueous solution of sodium hydroxide at an amount of 2.9 mol of sodium hydroxide per mol of anhydroglucose units was added over a time period of 45 min. The rate of addition was 0.064 mol of sodium hydroxide per mol of anhydroglucose units per minute. After the second-stage addition was completed the contents of the reactor were heated up to 80° C. in 20 min and then kept at a temperature of 80° C. for 120 min.

After the reaction, the reactor was vented and cooled down to about 50° C. The contents of the reactor were removed and transferred to a tank containing hot water. The crude methylcellulose was then neutralized with formic acid and washed chloride free with hot water (assessed by $AgNO_3$ flocculation test), cooled to room temperature and dried at 55° C. in an air-swept drier, and subsequently ground. The methylcellulose had a DS(methyl) of 1.88 (30.9 wt. % methoxyl), a mol fraction (26-Me) of 0.3276±0.0039, a mol fraction (23-Me) of 0.0642±0.0060, an s23/s26 of 0.20±0.02, and a steady-shear-flow viscosity $\eta(5° C., 10\ s^{-1}$, 2 wt. % MC) of 5500 mPa·s. The properties of the methylcellulose were measured as described below.

Samples of the produced methylcellulose were partially depolymerized by a known procedure to obtain the methylcelluloses MC-1 to MC-4. Generally speaking, the ground samples are treated with gaseous hydrogen chloride at a temperature of about 85° C. About 1.5 g gaseous hydrogen chloride per kg of methylcellulose is used. The reaction period is adapted to the desired viscosity. Partial depolymerization of cellulose ethers using gaseous hydrogen chloride is generally known from European patent application EP 1 141 029 and the prior art cited therein. The partial depolymerization does not impact the DS(methyl) or the s23/s26. The properties of the methylcelluloses MC-1 to MC-4 were measured as described below.

Methylcellulose MC-5

A methylcellulose was used which is commercially available from The Dow Chemical Company under the Trademark Methocel™ SGA7C cellulose ether which had a DS(methyl) of 1.95 (about 31.9 wt. % methoxyl), and an s23/s26 of 0.29. The viscosity of MC-5, measured at 5° C. as described below, is listed in Table 2 below.

Comparative Methylcelluloses

Various grades of standard methylcelluloses were used for comparative purposes which are commercially available from The Dow Chemical Company under the Trademark Methocel™ A methylcellulose and which have a DS(methyl) of 1.9 (about 31.2 wt. % methoxyl), and an s23/s26 of 0.39. The viscosities of these commercially available methylcelluloses, measured at 5° C. as described below, are listed in Table 2 below.

To provide the methylcellulose that was used in Comparative Example C, commercially available Methocel™ A4M methylcellulose was subjected to molecular weight degradation using gaseous HCl as generally described for the production of Methylcellulose MC-1 to MC-4 above. Degradation duration and temperature as well as amount of HCl were adjusted to the viscosity target of about 3 mPa·s.

Determination of s23/s26 of Methylcellulose

The approach to measure the ether substituents in methylcellulose is generally known. See for example the approach described in principle for Ethyl Hydroxyethyl Cellulose in Carbohydrate Research, 176 (1988) 137-144, Elsevier Science Publishers B.V., Amsterdam, DISTRIBUTION OF SUBSTITUENTS IN O-ETHYL-O-(2-HYDROXYETHYL)CELLULOSE by Bengt Lindberg, Ulf Lindquist, and Olle Stenberg.

Specifically, determination of s23/s26 was conducted as follows: 10-12 mg of the methylcellulose were dissolved in 4.0 mL of dry analytical-grade dimethyl sulfoxide (DMSO) (Merck, Darmstadt, Germany, stored over 0.3 nm molecular sieve beads) at about 90° C. with stirring and then cooled to room temperature. The solution was stirred at room temperature over night to ensure complete solubilization/dissolution. The entire perethylation including the solubilization of the methylcellulose was performed using a dry nitrogen atmosphere in a 4 mL screw cap vial. After solubilization, the dissolved methylcellulose was transferred to a 22-mL screw-cap vial to begin the perethylation process. Powdered sodium hydroxide (freshly pestled, analytical grade, Merck, Darmstadt, Germany) and ethyl iodide (for synthesis, stabilized with silver, Merck-Schuchardt, Hohenbrunn, Germany) were introduced in a thirty-fold molar excess relative to the level of anhydroglucose units in the methylcellulose, and the mixture was vigorously stirred under nitrogen in the dark for three days at ambient temperature. The perethylation was repeated with addition of the threefold amount of the reagents sodium hydroxide and ethyl iodide compared to the first reagent addition, and stirring at room temperature was continued for an additional two days. Optionally, the reaction mixture could be diluted with up to 1.5 mL DMSO to ensure good mixing during the course of the reaction. Next, five mL of 5% aqueous sodium thiosulfate solution was poured into the reaction mixture, and the mixture was then extracted three times with 4 mL of dichloromethane. The combined extracts were washed three times with 2 mL of water. The organic phase was dried with anhydrous sodium sulfate (about 1 g). After filtration, the solvent was removed with a gentle stream of nitrogen, and the sample was stored at 4° C. until needed.

Hydrolysis of about 5 mg of the perethylated samples was performed under nitrogen in a 2-mL screw-cap vial with 1 mL of 90% aqueous formic acid under stirring at 100° C. for 1 hour. The acid was removed in a stream of nitrogen at 35-40° C. and the hydrolysis was repeated with 1 mL of 2M aqueous trifluoroacetic acid for 3 hours at 120° C. in an inert nitrogen atmosphere with stirring. After completion, the acid was removed to dryness in a stream of nitrogen at ambient temperature using ca. 1 mL of toluene for co-distillation.

The residues of the hydrolysis were reduced with 0.5 mL of 0.5-M sodium borodeuteride in 2N aqueous ammonia solution (freshly prepared) for 3 hours at room temperature with stirring. The excess reagent was destroyed by dropwise addition of about 200 μL of concentrated acetic acid. The resulting solution is evaporated to dryness in a stream of nitrogen at about 35-40° C. and subsequently dried in vacuum for 15 min at room temperature. The viscous residue was dissolved in 0.5 mL of 15% acetic acid in methanol and evaporated to dryness at room temperature. This was done five times and repeated four additional times with pure methanol. After the final evaporation, the sample was dried in vacuum overnight at room temperature.

The residue of the reduction was acetylated with 600 μL of acetic anhydride and 150 μL of pyridine for 3 hrs at 90° C. After cooling, the sample vial was filled with toluene and evaporated to dryness in a stream of nitrogen at room temperature. The residue was dissolved in 4 mL of dichloromethane and poured into 2 mL of water and extracted with 2 mL of dichloromethane. The extraction was repeated three times. The combined extracts were washed three times with 4 mL of water and dried with anhydrous sodium sulfate. The dried dichloromethane extract was subsequently submitted to GC analysis. Depending on the sensitivity of the GC system, a further dilution of the extract could be necessary.

Gas-liquid (GLC) chromatographic analyses were performed with Agilent 6890N type of gas chromatographs (Agilent Technologies GmbH, 71034 Boeblingen, Germany) equipped with Agilent J&W capillary columns (30 m, 0.25-mm ID, 0.25-μm phase layer thickness) operated with 1.5-bar helium carrier gas. The gas chromatograph was programmed with a temperature profile that held constant at 60° C. for 1 min, heated up at a rate of 20° C./min to 200° C., heated further up with a rate of 4° C./min to 250° C., and heated further up with a rate of 20° C./min to 310° C. where it was held constant for another 10 min. The injector temperature was set to 280° C. and the temperature of the flame ionization detector (FID) was set to 300° C. Exactly 1 μL of each sample was injected in the splitless mode at 0.5-min valve time. Data were acquired and processed with a LabSystems Atlas work station.

Quantitative monomer composition data were obtained from the peak areas measured by GLC with FID detection. Molar responses of the monomers were calculated in line with the effective carbon number (ECN) concept but modified as described in the table below. The effective carbon number (ECN) concept has been described by Ackman (R. G. Ackman, J. Gas Chromatogr., 2 (1964) 173-179 and R. F. Addison, R. G. Ackman, J. Gas Chromatogr., 6 (1968) 135-138) and applied to the quantitative analysis of partially alkylated alditol acetates by Sweet et. Al (D. P. Sweet, R. H. Shapiro, P. Albersheim, Carbohyd. Res., 40 (1975) 217-225).

ECN Increments Used for ECN Calculations:

| Type of carbon atom | ECN increment |
| --- | --- |
| hydrocarbon | 100 |
| primary alcohol | 55 |
| secondary alcohol | 45 |

In order to correct for the different molar responses of the monomers, the peak areas were multiplied by molar response factors MRFmonomer which are defined as the response relative to the 2,3,6-Me monomer. The 2,3,6-Me monomer was chosen as reference since it was present in all samples analyzed in the determination of s23/s26.

MRFmonomer=ECN2,3,6-Me/ECNmonomer

The mol fractions of the monomers were calculated by dividing the corrected peak areas by the total corrected peak area according to the following formulas:
(1) s23 is the sum of the molar fractions of anhydroglucose units which meet the following condition [the two hydroxy groups in the 2- and 3-positions of the anhydroglucose unit are substituted with methyl groups, and the 6-position is not substituted (=23-Me)]; and
(2) s26 is the sum of the molar fractions of anhydroglucose units which meet the following condition [the two hydroxy groups in the 2- and 6-positions of the anhydroglucose unit are substituted with methyl groups, and the 3-position is not substituted (=26-Me)].

Determination of the DS(Methyl) a Methylcellulose

The determination of the % methoxyl in methylcellulose was carried out according to the United States Pharmacopeia (USP34). The values obtained were % methoxyl. These were subsequently converted into degree of substitution (DS) for methyl substituents. Residual amounts of salt were taken into account in the conversion.

Production of a 2% Pure Aqueous Solution of the Methylcellulose

To obtain a 2% aqueous solution of methylcellulose, 3 g of milled, ground, and dried methylcellulose (under consideration of the water content of the methylcellulose) were added to 147 g of tap water (temperature 20-25° C.) at room temperature while stirring with an overhead lab stirrer at 750 rpm with 3-wing (wing=2 cm) blade stirrer. The solution was then cooled to about 1.5° C. After the temperature of 1.5° C. was reached the solution was stirred for 180 min at 750 rpms. Prior to use or analysis, the solution was stirred for 15 min at 100 rpm in an ice bath.

Determination of the Viscosity of Methylcellulose

The steady-shear-flow viscosity $\eta(5°$ C., $10\ s^{-1}$, 2 wt. % MC) of an aqueous 2-wt. % methylcellulose solution was measured at 5° C. at a shear rate of $10\ s^{-1}$ with an Anton Paar Physica MCR 501 rheometer and cup and bob fixtures (CC-27).

Determination of the Viscosity of Aqueous Solutions for Application to a Mucosa

The viscosities of aqueous solutions for application to a mucosa were measured using an ARES RFS3 rheometer with cup and bob fixtures (TA-Instruments) at 5° C. and at a shear rate of $10\ s^{-1}$.

Determination of the Gelation Temperature of Aqueous Compositions Comprising Methylcellulose Rheology measurements of aqueous solutions comprising MC and optionally a tonicity-adjusting agent, such as a buffering agent, and/or a physiologically active agent were conducted with an Ares RFS3 rheometer (TA-Instruments) with cup and bob fixtures. Seventeen milliliters of solution were transferred to the cup fixture and the gap set to 5 mm. The sample was heated at a rate of 1° C. per minute over a temperature range from 10 to 50° C. with a constant strain of 2% and a constant angular frequency of 5 radians per second. The storage modulus G', which was obtained from the rheology measurements, represents the elastic properties of the solution.

The obtained data of the storage modulus G', which was obtained from the oscillation measurements, was first logarithmized and normalized to G' (min) to zero and G' (max) to 100. Linear regression curves were fitted to subsets of these storage modulus data (increments of 5 data points). The regression curve with the steepest slope was chosen to identify the inflection point of the curve. The intersection with the x-axis is reported as gelation temperature extrapolated from inflection point.

FIG. 1 illustrates how to determine the gelation temperature of the composition of Example 8. The gelation temperature of other compositions of the present invention and of comparative compositions can be determined in the same manner.

Preparation of Aqueous Solutions for Application to the Nasal Mucosa

Concentrated MC solutions having the concentrations as listed in Table 1 below were prepared by adding a corresponding amount of dry methylcellulose powder to water which had an initial temperature of 25° C. using a Yamato LT 400 lab overhead mixer to achieve a good dispersion. The mixture of the MC and water was cooled to 2° C. within 20 minutes while stirring at the same speed. After the mixture of MC and water reached the temperature of 2° C., the mixture was stirred for one additional hour at this temperature and was then subjected to high shear using a Silverson L4-R high-shear mixer (rotor stator) running at 5000 rpm. These solutions were stored overnight in a refrigerator.

TABLE 1

| MC type | MC concentration in concentrated MC solution |
|---|---|
| MC-1 | 7% |
| Methocel A15 | 4% |
| MC-2 | 4% |
| MC-3 | 2% |
| Methocel A4C | 4% |
| MC-4 | 2% |
| MC-5 | 4% |
| Partially depolymerized Methocel A of Comparative Example C | 2% |

A concentrated MC solution from the refrigerator was mixed either with water or with a concentrated aqueous solution of a tonicity-adjusting agent and/or an active pharmaceutical ingredient (API) from the refrigerator by the use of a stirrer until a homogenous solution was achieved. Acetaminophen was used as API. During this additional mixing the solution temperature was still cold and a temperature above 7° C. was not reached. The concentration of the tonicity-adjusting agent and/or the API in the concentrated aqueous solution was chosen to achieve the desired concentration in the resulting mixture at the chosen mixing ratio. In the resulting mixture the tonicity-adjusting agent was the salt in a pH 6.5 phosphate buffered solution (PBS) which comprised 0.65 weight percent sodium chloride and 0.25 weight percent sodium phosphate in deionized water. For example, the aqueous solution of Example 6 was prepared by mixing equal parts of 2 wt. % MC-4 with a solution containing 1.3 wt. % sodium chloride and 0.5 wt. % sodium phosphate to generate the 1 wt. % MC solution in phosphate buffered saline (0.65% sodium chloride, 0.25% sodium phosphate). The aqueous solutions of all Examples and Comparative Examples were fully soluble, clear solutions and were stored in the refrigerator until the characterization had been performed.

The chemical compositions of the aqueous solutions, their gelation temperatures and their viscosities are listed in Table 2 below.

tion with a tonicity-adjusting agent has a lower gelation temperature than a composition that comprises the same methylcellulose alone. The composition of Comparative Example A gels above the normal temperature of a human mucosa and, accordingly, does not have same benefits as the composition of Example 1. Comparative Example B illustrates that the presence of an active pharmaceutical ingredient (API) does not necessarily reduce the gelation temperature of the composition.

Examples 2 and 3 illustrate that the gelation temperature can be further decreased by increasing the concentration of the methylcellulose. Example 5 illustrates that the concentration of the methylcellulose can be lowered while still achieving a gelation temperature that is sufficiently low such that the composition can be efficiently applied to, e.g., an oral mucosa.

Comparative Examples C and D illustrate that a standard methylcellulose of similar viscosity (measured as 2 wt. % aqueous solution) does not have the same advantages as a methylcellulose with s23/s26 of 0.36 or less, even not in combination with a tonicity-adjusting agent. An aqueous solution comprising a standard methylcellulose in combination with a tonicity-adjusting agent does not gel at the temperature of a mucosa.

The comparison between Example 6 and 7 on the one hand and Comparative Example E on the other hand again illustrates that a composition which comprises methylcellulose with s23/s26 of 0.36 or less in combination with a tonicity-adjusting agent has a lower gelation temperature than a composition that comprises the same methyl cellulose alone. Methylcellulose MC-4 has a viscosity that is 1000 times as high as the one of MC-1. Accordingly, the discussed difference between comparative compositions comprising the methylcellulose with the specified s23/s26 alone and compositions of the present invention which comprise the methylcellulose in combination with a tonicity-adjusting agent can be observed over a wide viscosity range. Comparative Example F again illustrates that a standard meth-

TABLE 2

| (Comp). Example | MC | s23/s26 of MC | MC viscosity, 2 wt. % in water at 5° C., mPa·s | MC concentration, wt.-% | liquid | API, wt.-% | Gelation Temperature, ° C. | Solution viscosity, mPa·s at 5° C. |
|---|---|---|---|---|---|---|---|---|
| A | MC-1 | 0.20 | 3 | 1 | water | — | 38 | nm |
| B | MC-1 | 0.20 | 3 | 1 | water | 0.5 | 38 | nm |
| 1 | MC-1 | 0.20 | 3 | 1 | PBS | — | 34 | nm |
| 2 | MC-1 | 0.20 | 3 | 2 | PBS | — | 33 | 5 |
| 3 | MC-1 | 0.20 | 3 | 2 | PBS | 0.5 | 31 | 5 |
| C | Part. depolym. Methocel A | 0.39 | 3 | 2 | PBS | — | 43 | 5 |
| D | Methocel A15 | 0.39 | 26 | 2 | PBS | 0.5 | 47 | 28 |
| 5 | MC-1 | 0.20 | 3 | 0.75 | PBS | — | 36 | nm |
| E | MC-4 | 0.20 | 3000 | 1 | water | — | 26 | nm |
| 6 | MC-4 | 0.20 | 3000 | 1 | PBS | — | 22 | 218 |
| 7 | MC-4 | 0.20 | 3000 | 1 | PBS | 0.5 | 23 | 228 |
| F | Methocel A4M | 0.39 | 7580 | 1 | PBS | 0.5 | >50 | 642 |
| G | MC-3 | 0.20 | 742 | 1 | water | — | 28 | nm |
| 8 | MC-3 | 0.20 | 742 | 1 | PBS | — | 25 | 81 |
| H | Methocel A4C | 0.39 | 814 | 1 | PBS | 0.5 | >50 | 94 |
| I | MC-5 | 0.29 | 1044 | 2 | water | — | 36 | 1044 |
| 9 | MC-5 | 0.29 | 1044 | 2 | PBS | 0.5 | 34 | 1196 |
| 10 | MC-2 | 0.20 | 40 | 2 | PBS | — | 26 | 46 |
| 11 | MC-2 | 0.20 | 40 | 2 | PBS | 0.5 | 26 | 52 | nm: not measured

The comparison between Example 1 and Comparative Example A illustrates that a composition which comprises methylcellulose with a s23/s26 of 0.36 or less in combina- ylcellulose of similar viscosity does not have the same advantages as a methylcellulose with a s23/s26 of 0.36 or less, even not in combination with a tonicity-adjusting agent.

The comparison between Example 8 and Comparative Example G again illustrates that a composition which comprises methylcellulose with s23/s26 of 0.36 or less in combination with a tonicity-adjusting agent has a lower gelation temperature than a composition that comprises the same methyl cellulose alone. Comparative Example H again illustrates that a standard methylcellulose of similar viscosity does not have the same advantages as a methylcellulose with a s23/s26 of 0.36 or less, even not in combination with a tonicity-adjusting agent.

The compositions of Comparative Examples E and G have a sufficiently low gelation temperature to be effectively applied to the nasal mucosa. However, the finding of the present invention that the combination of an MC with a tonicity-adjusting agent lowers the gelation temperature even more provides additional flexibility when formulating compositions for application to a mucosa. It is known that reduction of the methylcellulose concentration or choosing a methylcellulose of lower viscosity increases the gelation temperature. The present invention increases the flexibility to reduce the methylcellulose concentration or to choose a methylcellulose of lower viscosity in combination with a tonicity-adjusting agent while still providing a composition that gels at the temperature of a mucosa or lower, as illustrated by Examples 1-5 in comparison with comparative Examples A-D.

The comparison between Example 9 and Comparative Example I again illustrates the above-mentioned advantage of the present invention. Examples 10 and 11 illustrate compositions of the present invention with a methylcellulose of yet another viscosity.

Comparative Examples C, D, F and H illustrate aqueous solutions comprising standard methylcelluloses in a wide range of different viscosities in combination with PBS as a tonicity-adjusting agent. The compositions of Comparative Examples C, D, F and H all gel above the normal temperature of a human mucosa and, accordingly, do not have same benefits as the compositions of the Examples of the present invention.

The invention claimed is:

1. A composition selected from the group consisting of nasal drops and nasal sprays comprising a physiologically active agent, a tonicity-adjusting agent, a methylcellulose, and a liquid diluent, wherein the methylcellulose has anhydroglucose units joined by 1-4 linkages wherein hydroxy groups of anhydroglucose units are substituted with methyl groups such that s23/s26 is 0.24 or less, wherein s23 is the molar fraction of anhydroglucose units wherein only the two hydroxy groups in the 2- and 3-positions of the anhydroglucose unit are substituted with methyl groups and wherein s26 is the molar fraction of anhydroglucose units wherein only the two hydroxy groups in the 2- and 6-positions of the anhydroglucose unit are substituted with methyl groups, the tonicity-adjusting agent is sodium chloride, potassium chloride, calcium chloride, a buffering agent, xylitol, glycerin, mannitol or sorbitol, and the liquid diluent comprises from 90 to 100 weight percent of water and no more than 10 weight percent of organic liquid diluent, based on the total weight of organic liquid diluent and water.

2. The composition of claim 1 comprising the methylcellulose, wherein hydroxy groups of anhydroglucose units are substituted with methyl groups such that s23/s26 is 0.22 or less.

3. The composition of claim 1 wherein the methylcellulose has a DS (methyl) of from 1.55 to 2.25.

4. The composition of claim 1, wherein the methylcellulose has a viscosity of from 3 to 3000 mPa·s, measured as 2 wt. % aqueous solution at 5° C. at a shear rate of 10 $s^{-1}$.

5. The composition of claim 1 exhibiting a gelation temperature of from 18 to 37° C.

6. The composition of claim 1 wherein the physiologically active agent is selected from one or more drugs or one or more physiologically active agents which are useful for nutritional purposes.

7. A container comprising the composition of claim 1, wherein the container is designed to release the composition by spraying or as drops.

8. A method of transmucosal administration of a physiologically active agent to an individual wherein the composition of claim 1 is applied to a mucosa of the individual.

* * * * *